United States Patent [19]

Stoss

[11] 4,371,703
[45] Feb. 1, 1983

[54] PROCESS FOR THE PRODUCTION OF ISOSORBIDE-5-NITRATE

[75] Inventor: Peter Stoss, Illertissen, Fed. Rep. of Germany

[73] Assignee: Heinrich Mack Nachf. Chem-Parm. Fabrik, Illertissen, Fed. Rep. of Germany

[21] Appl. No.: 337,903

[22] Filed: Jan. 7, 1982

[30] Foreign Application Priority Data

Jan. 29, 1981 [DE] Fed. Rep. of Germany ....... 3102947

[51] Int. Cl.$^3$ .......................................... C07D 493/04
[52] U.S. Cl. ................................................... 549/464
[58] Field of Search ........................................ 549/464

[56] References Cited

U.S. PATENT DOCUMENTS 4,065,488  12/1977  Chou et al. .................... 424/298 X

FOREIGN PATENT DOCUMENTS 2751934  8/1978  Fed. Rep. of Germany .
2903927  6/1980  Fed. Rep. of Germany .

OTHER PUBLICATIONS

Sisenwine et al., J. Pharmacol. Exp. Ther., 176,296, (1971).
Down et al., J. Pharm. Sci. 63,1147, (1974).
Chasseaud et al., Eur. J. Clin. Pharmacol., 8,157, (1975).
Wendt, J. Pharmacol. Exp. Ther. 180,732, (1972).
Bogaert et al., Naunyn–Schmiedebergs Arch. Pharmacol., 275,339, (1972).
Stauch et al., Verh. Dtsch. Ges Kreislavfforsch., 41,182, (1975).
Michel, Herz-Kreislauf, 8,444, (1976).
Csizmadia et al., Photochem. Photobiol., 4,657, (1965).
Anteunis et al., Org. Magnet. Resonance 3, 693, (1971).
Buck et al., Carbohydrates Res., 2,122, (1966).

Primary Examiner—Richard Raymond
Attorney, Agent, or Firm—Charles J. Knuth; Peter C. Richardson; Harold W. Ordway

[57] ABSTRACT

This invention relates to a process for the production of isosorbide-5-nitrate comprising (a) subjecting an acylation mixture of isosorbide containing varying proportions of isosorbide, isosorbide-2-acylate, isosorbide-5-acylate and/or isosorbide-2,5-diacylate, or pure isosorbide-5-acylate or an equimolar mixture of isosorbide-2,5-diacylate and isosorbide to a transacylation reaction in the presence of a catalyst and removing the isosorbide-2-acylate present from the reaction mixture by fractional distillation;

(b) optionally subjecting the separated isosorbide-2-acylate to a further purification step;

(c) esterifying the obtained isosorbide-2-acylate with nitric acid; and (d) partially hydrolyzing the obtained isosorbide-2-acylate-5-nitrate.

4 Claims, No Drawings

PROCESS FOR THE PRODUCTION OF ISOSORBIDE-5-NITRATE

BACKGROUND OF THE INVENTION

The present invention relates to a novel, advantageous process for the production of isosorbide-5-nitrate (1,4-3,6-dianhydroglucitol-5-nitrate) of formula 1.

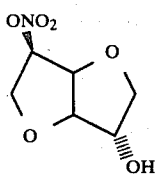

Isosorbide-5-nitrate (5-ISM) is a well-known compound whose therapeutical application has recently been intensively investigated. The starting point of this interest was the observation that isosorbide-2,5-dinitrate (ISD), a well established substance used in the treatment of coronary diseases, is rapidly metabolized in the organism and that isosorbide-2-nitrate (2-ISM) and isosorbide-5-nitrate (5-ISM) occur as metabolites. [S. F. Sisenwine and H. W. Ruelius, J. Pharmacol. Exp. Ther. 176,269 (1971); W. H. Down et al., J. Pharm. Sci. 63,1147 (1974); L. F. Chasseaud et al., Eur. J. Clin. Pharmacol. 8,157 (1975)].

Moreover, it has been shown that the metabolites 2-ISM and 5-ISM in principle have the same effect as the mother substance ISD [R. L. Wendt, J. Pharmacol. Exp. Ther. 180,732 (1972); M. G. Bogaert et al., Naunyn-Schmiedebergs Arch. Pharmacol. 75, 339 (1972); M. Stauch et al., Verh. Dtsch. Ges Kreislaufforsch. 41, 182 (1975); D. Michel, Herz-Kreislauf 8,444 (1976)].

Compared with ISD it has been further observed that 2-ISM and 5-ISM are advantageously distinguished by various therapeutically important parameters such as resorption behaviour, half life, toxicity, oral applicability and the like. Instead of ISD it may therefore be expedient to administer the mononitrates, especially isosorbide-5-nitrate, to treat heart diseases such as angina pectoris. This application, however, requires an economic, technically feasible source of the pure substances.

The 5-ISM syntheses that are presently available are not satisfactory with respect to technical practicability, yield and costs. The following methods are known:

Isosorbide is directly nitrated whereby a mixture of ISD, 2-ISM, 5-ISM and unchanged isosorbide, of varying composition, results. This mixture has to be separated into its individual components by time consuming and costly chromatographic separation procedures that cannot be carried out on an industrial scale. The yield of 5-ISM obtained in this way is so small and the isolation method is so time consuming and expensive that no practical importance can be attached to this method [I. G. Csizmadia and L. D. Hayward, Photochem. Photobiol. 4,657 (1965)].

Another procedure according to which isosorbide is first converted into the 2,5-dinitrate and then partially hydrolyzed, results again in the mixture of ISD, 2-ISM and isosorbide mentioned above, the separation and isolation of which is not economically viable [M. Anteunis et al., Org. Magnet. Resonance 3, 693 (1971)].

DOS No. 2 751 934 and the corresponding U.S. Pat. No. 4,065,488 describe the following procedure: Isosorbide is acylated with an acid chloride or an acid anhydride whereby a mixture of isosorbide-2-acylate, isosorbide-5-acylate, isosorbide-2,5-diacylate and isosorbide is obtained. Isosorbide is extracted from this mixture in order to prevent the formation of ISD, a potentially explosive substance, in the subsequent nitration step. The remaining mixture of isosorbide-2-acylate, isosorbide-5-acylate and isosorbide-2,5-diacylate is nitrated with nitric acid yielding a mixture of isosorbide-5-acylate-2-nitrate, isosorbide-2-acylate isosorbide-5-nitrate and isosorbide-2,5-diacylate. By a selective hydrolysis a mixture of isosorbide-2-nitrate, isosorbide-5-nitrate and isosorbide results. The latter has to be removed again by extraction before isosorbide-2-nitrate is isolated as the main component from the remaining residue by crystallizing from suitable solvents. Isosorbide-5-nitrate remains in the mother liquors. There is a lack of any instructions concerning its isolation.

All previously mentioned procedures are characterized by the fact that a selective preparation of isosorbide-5-nitrate is not possible because of the formation of mixtures which then have to be separated into their individual components by suitable separation procedures. This is, however, a costly and time consuming process. The desired final product can only be obtained in a poor yield and thus an economical production is not possible.

The first process for a selective preparation of isosorbide-5-nitrate was recently published in DAS No. 2 903 927. According to this process, isomannide is converted into the corresponding isomannide-2-ester by means of a halide or anhydride of a suitable sulfonic acid or carboxylic acid. The reaction of the isomannide-2-ester with an alkaline salt or an ammonium salt of a benzoic acid or with tetrabutyl ammonium acetate or tetrabutyl ammonium formate provides an isosorbide-2-ester. This is then esterified in a known manner with nitric acid and the resultant isosorbide-2-ester-5-nitrate is then partially hydrolyzed, under cleavage of the 2-ester group, thus yielding isosorbide-5-nitrate. This process possesses advantages over previously known ones in as much as only one defined product results. With respect to expense and economy, however, this procedure is unsuitable. The starting material, isomannide, is at present essentially more difficult to obtain and also much more expensive than isosorbide. Moreover, this procedure consists of four steps and is therefore labour and apparatus intensive as well as time consuming. Finally, the overall yield of this four step method is less than 50% of the theoretical yield.

It is generally known that the following main procedures can be considered for the acylation of isosorbide:
1. esterification of isosorbide with acids
2. transesterification of isosorbide with acid esters
3. acylation of isosorbide with acyl halides
4. acylation of isosorbide with anhydrides As a diol, isosorbide has two points of attack. Accordingly any acylation attempt results in a mixture of isosorbide, isosorbide-2-acylate, isosorbide-5-acylate and isosorbide-2,5-diacylate with varying amounts of the individual components. The composition of the product mixture varies depending on the production method and the reaction conditions. Results of systematic investigations of this subject are not yet available; only some individual observations have been reported.

For example, DOS No. 2 751 934 mentioned previously describes a mixture of the four possible components obtained by acylation of isosorbide with acid anhydrides in the presence of acidic catalysts but does not describe the composition of the mixture.

The conversion of isosorbide with 1 mol of acetic acid anhydride in pyridine produced isosorbide-2-2- and 5-monoacetate in a ratio of approx. 1.7:1 as well as isosorbide-2,5-diacetate as the main product (K. S. Buck et al., Carbohydrates Res. 2, 122 (1966)). In the presence of pyridine hydrochloride a product ratio of 2-acetate/5-acetate of approx. 1:3.6 was achieved, however, again in a lesser amount, along with 2,5-diacetate. In neither of the isosorbide monoacetates did acyl migration occur due to the influence of pyridine, with or without the addition of pyridine hydrochloride.

Therefore there is still a demand for manufacturing procedures which provide, over a few steps, isosorbide-5-nitrate in improved yields and in which inexpensive starting materials are used.

SUMMARY OF THE INVENTION

It was therefore surprising and not foreseeable that under similar conditions as cited in the above literature, a migration of the acyl group in the molecule was achieved. By using the process of the present invention it is possible to effect a catalytic transacylation whereby independent of the original product ratio, a mixture always results which has an almost constant product ratio in which isosorbide-2-acylate predominates. The starting material used for the transacylation may consist of an acylation mixture, obtained according to generally known procedures, with varying amounts of isosorbide, isosorbide-2-acylate, isosorbide-5-acylate and isosorbide-2,5-diacylate, whereby the amounts of the individual components may vary greatly. It may also consist of an equimolar mixture of isosorbide and isosorbide-2,5-diacylate or of pure isosorbide-5-acylate. If the isosorbide-2-acylate is continually distilled off from the equilibrated transacylation mixture, then the equilibrium of this mixture in the distillation vessel is continually being altered, under the catalytic effect to the benefit of the isosorbide-2-acylate. Thus, isosorbide-2-acylate of good purity is obtained in high yields. Accordingly, the distillative separation of the isosorbide-2-acylate is carried out using a column with a sufficient number of theoretical plates. In this way the isosorbide-2-acylate content of the distillate may be raised to yield a product of sufficiently high purity to enable it to be used directly, or after a further purification procedure, for example recrystallization or extraction, in the subsequent process steps. Said further purification may be effected also by a further distillation.

Under the term "acyl groups" that are subject to the catalytic transacylation according to the invention, straight-chained or branched aliphatic carboxylic acid moieties having from one to six carbon atoms are meant, such as formyl, acetyl, propionyl, butyryl, valeryl, capronyl, isobutyryl, isovaleryl and pivaloyl.

Preferred catalysts for use in the present process are sulfonic acids, inorganic acids, metal carbonates or ammonium carbonates, metal or ammonium salts of straight-chained or branched lower alkyl carboxylic acids with 1 to 6 carbon atoms, alkaline metal hydrides, alkaline metal earth hydrides, alkaline metal alcoholates or alkaline metal earth alcoholates, metal oxides or metal hydroxides, organic nitrogen compounds or phase transfer catalysts in the form of quaternary ammonium and phosphonium compounds.

DETAILED DESCRIPTION OF THE INVENTION

The process of this invention is carried out as follows: 0.001 to 0.01 mol equivalents of the catalyst is added to an acylation mixture of isosorbide, isosorbide-2-acylate, isosorbide-5-acylate, isosorbide-2,5-diacylate of varying composition obtained according to generally known procedure, or an equimolar mixture of isosorbide and isosorbide-2,5-diacylate, or pure isosorbide-5-acylate and distilled in a distilling vessel with an affixed column. Thereby isosorbide-2-acylate preferentially distills off. In the distilling mixture a continuous transacylation occurs so that the isosorbide-2-acylate that is removed from the equilibrium is constantly being generated and enriches itself in the distillate. Depending on the kind of catalyst, the quality of the column used, the reflux ratio and the like; isosorbide-2-acylate obtained in this way in a purity of approx. 85 to 95% and the yield is almost quantitative.

The transacylation is effected by a great number of different catalysts. In particular the following catalysts are suitable: sulfonic acids, inorganic acids, ammonium- and metal salts of carbonic acid as well as ammonium- and metal salts of straight-chained or branched lower alkyl carboxylic acids having 1 to 6 carbon atoms. The metals used for the salt formation may belong to the group of alkaline or alkaline earth metals as well as other groups of the periodic system. The following catalysts may also be used: alkaline metal hydrides and alkaline metal earth hydrides, alkaline metal alcoholates and alkaline metal earth alcoholates, metallic oxides and metallic hydroxides, organic nitrogen compounds as well as phasetransfer catalysts from the group of the quaternary ammonium and phosphonium compounds.

Suitable catalysts, for example, are methane sulfonic acid, benzene sulfonic acid, p-toluene sulfonic acid, phosphoric acid, sodium acetate, potassium acetate, ammonium acetate, calcium acetate, barium acetate, lead acetate, cobalt acetate, sodium propionate, ammonium butyrate, sodium isobutyrate, potassium capronate, potassium carbonate, sodium carbonate, calcium carbonate, sodium hydride, potassium hydride, calcium hydride, sodium methylate, sodium ethylate, potassium-tert. butylate, aluminum oxide, calcium oxide, sodium hydroxide, potassium hydroxide, calcium hydroxide, triethylamine, 4-dimethylaminopyridine, triphenylamine, cetyl trimethyl ammonium bromide, tetrabutyl ammonium hydrogen sulfate, benzyl triethyl ammonium chloride, tetraethyl ammonium hydroxide, benzyl triphenyl phosphonium bromide and others.

The isosorbide-2-acylate obtained in this way may be additionally purified by recrystallization and/or extraction resulting in an isosorbide-2-acylate with a purity exceeding 99%. The mother liquors resulting from this purification procedure which, in addition to a small amount of isosorbide-2-acylate, containing mainly isosorbide, isosorbide-5-acylate and isosorbide-2,5-diacylate, may again be transacylated, e.g. by recharging it into the distillation vessel or by adding it to a new batch. In this way an almost quantitative conversion to isosorbide-2-acylate is obtained.

The process is continued by esterification of the very pure isosorbide-2-acylate, readily and economically available for the first time by the present invention, with nitric acid by known methods whereby the isosorbide-2-acylate-5-nitrate obtained is not contaminated by any by-products. In the next step the 2-acyl group is selectively cleaved by alkaline hydrolysis or transesterification by known methods using for example sodium hydroxide or potassium hydroxide in an organic or aqueous alcoholic medium, or in a lower alcohol in the presence of an alkaline alcoxide to produce pure isosorbide-5-nitrate.

Compared with the initially mentioned, well-known procedures, the advantage of the process of this invention is that the easier accessible and considerably cheaper isosorbide can be used as the starting material. Moreover, this process comprises only three steps that are technically easy to carry out. Finally, the overall yield of this procedure is essentially higher than those of the previously mentioned procedures.

The following examples illustrate further the process of the invention:

EXAMPLE 1

To 146 g (1 mol) of isosorbide and 230 g (1 mol) of isosorbide-2,5-diacetate, 2 g of sodium methoxide are added and the mixture is distilled under vacuum over a column. Thereby a distillate of 360 g is recovered with a boiling point of 98°–100° C./0.1 mbar and which readily crystallizes in the receiving vessel. The substance consists mainly of isosorbide-2-acetate (85–95%) with small amounts of isosorbide, isosorbide-2,5-diacetate and traces of isosorbide-5-acetate. By a single recrystallization, e.g. from acetone, isosorbide-2-acetate is obtained with a purity of more than 99%; M.P. 80° C. After removal of the solvent the mother liquor obtained from the recrystallization procedure is again transacylated or added to the next batch, respectively, whereby an almost quantitative formation of isosorbide-2-acetate is obtainable.

EXAMPLE 2

146 g (1 mol) of isosorbide, 60 g (1 mol) of acetic acid and 1 g of p-toluene sulfonic acid are refluxed in 250 ml of benzene using a water separator until the theoretical quantity of water (18 ml) has been separated. The mixture obtained, consisting of approx. equal portions of isosorbide, isosorbide 2-acetate, isosorbide-5-acetate and isosorbide-2,5-diacetate, is subjected to transacylation by the addition of 2 g of potassium carbonate, and distilled. 180 g of a distillate that solidifies crystalline and which composition corresponds to the one described in example 1, distills at 98°–100° C./0.1 mbar.

EXAMPLE 3

188 g (1 mol) of isosorbide-5-acetate are treated according to example 1 after adding 1 g of sodium hydride resulting in 180 g of a distillate with a comparable product composition.

EXAMPLE 4

At approx. 100° C., 102 g (1 mol) of acetic acid anhydride are added to 146 g (1 mol) of isosorbide and 1 g of sodium acetate. This mixture is heated for half an hour under reflux and the acetic acid formed is then removed under a water-pump vacuum up to a sump temperature of approx. 140° C. An analysis of the residue shows that isosorbide, isosorbide-2-acetate, isosorbide-5-acetate and isosorbide-2,5-diacetate are present in approximately equal proportions. By the following transacylation and distillation, according to example 1, 182 g of raw isosorbide-2-acetate are obtained. After recrystallizing from 200 ml of acetone 92 g of pure isosorbide-2-acetate with a M.P. of 80° C. are obtained. The residue (90 g) remaining after concentrating the filtrate is again subjected to transacylation after adding 0.5 g of sodium acetate whereby again an almost quantitative yield of raw isosorbide-2-acetate is achieved. From this, 43 g of pure isosorbide-2-acetate and 46 g residue are obtained as described above. By another distillation in the presence of sodium acetate it is possible to prepare from the 46 g residue, 44 g of raw isosorbide-2-acetate from which, by recrystallisation, 26 g of pure isosorbide-2-acetate can be isolated. In this way a total amount of 161 g of pure isosorbide-2-acetate is obtained corresponding to 83% of the theory and 18 g residue which may be used for further transacylations. By repeating the above mentioned procedure resp. by adding the remaining residue to the next acylation batch an almost quantitative yield of pure isosorbide-2-acetate can be obtained.

EXAMPLE 5

If the acetic acid described in example 2 or the acetic acid anhydride described in example 4 are replaced by the corresponding straight-chained or branched homologous carboxylic acids or carboxylic acid anhydrides, or if the acylation of isosorbide is carried out by means of the corresponding carboxylic acid halide or carboxylic acid ester, or, as described in example 1, a mixture of isosorbide and the corresponding isosorbide-2,5-diacylate, or, as described in example 3, pure isosorbide-5-acylate is the starting material, the following isosorbide-2-acylates are obtained after the catalytic transacylation in comparable qualities and yields according to the above mentioned examples:

| | |
|---|---|
| 2-formyl-isosorbide | M.P. 62° C. |
| 2-propionyl-isosorbide | M.P. 47° C. |
| 2-butyryl-isosorbide | M.P. 51–52° C. |
| 2-valeryl-isosorbide | M.P. 39–40° C. |
| 2-capronyl-isosorbide | M.P. 57° C. |
| 2-isobutyryl-isosorbide | oily |
| 2-isovaleryl-isosorbide | oily |
| 2-pivaloyl-isosorbide | M.P. 58° C. |

EXAMPLE 6

A catalytic transacylation also takes place when the catalysts described in examples 1 to 4 are replaced by the following ones: methane sulfonic acid, benzene sulfonic acid, p-toluene sulfonic acid, phosphoric acid, ammonium acetate, potassium acetate, calcium acetate, barium acetate, nickel acetate, cobalt acetate, lead acetate, sodium propionate, ammonium butyrate, potassium isobutyrate, sodium capronate, sodium carbonate, calcium carbonate, potassium hydride, calcium hydride, sodium ethylate, potassium-tert. butylate, aluminum oxide, calcium oxide, sodium hydroxide, potassium hydroxide, calcium hydroxide, triethylamine, 4-dimethylamino-pyridine, triphenylamine, cetyl trimethyl ammonium bromide, tetrabutyl ammonium hydrogen sulfate, benzyl triethyl ammonium chloride, tetraethyl ammonium hydroxide, benzyl triphenyl phosphonium bromide.

Thus from 146 g (1 mol) of isosorbide and 230 g (1 mol) of isosorbide-2,5-diacetate, by the addition of 1–2 g of one of the catalysts mentioned above and treating this mixture according to example 1,340–365 g of a distillate that solidifies to crystals and shows the composition mentioned in example 1, are obtained.

EXAMPLE 7

While stirring and at a temperature of 5° to 10° C., 188 g of pure isosorbide-2-acetate are added gradually to a nitrating mixture prepared from 130 g of 65% nitric acid and 400 ml of acetic anhydride, with cooling. After having stirred at the same temperature for another hour the mixture is poured into 1 liter of water and extracted twice with 300 ml of methylene chloride. The combined organic phases are carefully washed with dilute aqueous sodium carbonate solution and then freed from the solvent. The residue is dissolved in 500 ml of methanol, 5 ml of a 35% methanolic sodium methoxide solution are added and the mixture is left to stand at room temperature until complete conversion has been established by thin layer chromatography (approx. 1 h). After neutralizing with acetic acid the solution is evaporated to dryness under vacuum and the residue is recrystallized from 300 ml of water. Yield: 160 g (85% of the theory) of isosorbide-5-nitrate, M.P. 93° C.

EXAMPLE 8

Using the same procedure as described in example 7, however, replacing the pure isosorbide-2-acetate by 188 g of raw isosorbide-2-acetate obtained from the distillation in examples 1 to 4, the residue, remaining after neutralizing and evaporating the methanolic solution to dryness, is dissolved in 500 ml of water at 40° C. and extracted with 100 ml of toluene/petroleum ether (1:1). The organic extract contains small quantities of isosorbide-2,5-dinitrate. The aqueous phase is concentrated to 400 ml, cooled down to 0° C. and the crystallized isosorbide-5-nitrate is suction filtered. In this way 135 g (71% of the theory) with a M.P. of 93° C. are obtained.

EXAMPLE 9

Instead of the isosorbide-2-acetate used in example 7 and 8, the straight-chained or branched, homologous isosorbide-2-acylates prepared according to example 5 are analogously subjected to the esterification with nitric acid and the subsequent partial hydrolysis whereby isosorbide-5-nitrate with a M.P. of 93° C. is obtained; yields between 70 and 85%.

I claim:

1. A process for the preparation of isosorbide-5-nitrate comprising
   (a) heating an acylation mixture of isosorbide, said mixture containing varying proportions of isosorbide, isosorbide-2-acylate, isosorbide-5-acylate and/or isosorbide-2,5-diacylate, or pure isosorbide-5-acylate or an equimolar mixture of isosorbide-2,5-diacylate and isosorbide, in the presence of a transacylation catalyst and separating isosorbide-2-acylate from said mixture by fractional distillation;
   (b) esterifying said isosorbide-2-acylate with nitric acid to form isosorbide-2-acylate-5-nitrate; and
   (c) Partially hydrolysing said isosorbide-2-acylate-5-nitrate to form isosorbide-5-nitrate.

2. A process according to claim 1 wherein said isosorbide acylate is isosorbide acetate.

3. A process according to claim 1, wherein the separated isosorbide-2-acylate is purified by recrystallization or extraction.

4. A process according to claim 1 wherein said transacylation catalyst is methane sulfonic acid, benzene sulfonic acid, p-toluene sulfonic acid, phosphoric acid, sodium acetate, potassium acetate, ammonium acetate, calcium acetate, barium acetate, lead acetate, cobalt acetate, sodium propionate, ammonium butyrate, sodium isobutyrate, potassium capronate, potassium carbonate, sodium carbonate, calcium carbonate, sodium hydride, potassium hydride, calcium hydride, sodium methylate, sodium ethylate, potassium-tert. butylate, aluminum oxide, calcium oxide, sodium hydroxide, potassium hydroxide, calcium hydroxide, triethylamine, 4-dimethylaminopyridine, triphenylamine, cetyl trimethyl ammonium bromide, tetrabutyl ammonium hydrogen sulfate, benzyl triethyl ammonium hydrogen sulfate, benzyl triethyl ammonium chloride, tetraethyl ammonium hydroxide or benzyl triphenyl phosphonium bromide.

* * * * *